United States Patent [19]
McBarnes, Jr. et al.

[11] Patent Number: 5,094,418
[45] Date of Patent: Mar. 10, 1992

[54] IV POLE

[75] Inventors: Robert L. McBarnes, Jr., Kalamazoo; Martin W. Stryker, Kalamazoo Township, Kalamazoo County, both of Mich.

[73] Assignee: Stryker Corporation, Kalamazoo, Mich.

[21] Appl. No.: 578,900

[22] Filed: Sep. 7, 1990

[51] Int. Cl.⁵ .................................. A47C 21/00
[52] U.S. Cl. ........................ 248/286; 5/658; 248/125; 248/308
[58] Field of Search .......... 248/282, 125, 286, 308, 248/188.5; 5/503, 508

[56] References Cited

U.S. PATENT DOCUMENTS

| | | | |
|---|---|---|---|
| 837,642 | 12/1906 | Powell | 5/503 X |
| 1,231,452 | 6/1917 | Sword | |
| 1,297,043 | 3/1919 | Travis | 5/508 |
| 1,704,979 | 3/1929 | Kusteele et al. | 248/286 X |
| 1,862,237 | 6/1932 | Pepler | |
| 1,865,757 | 7/1932 | Honsowetz | 248/286 |
| 2,654,484 | 10/1953 | Win et al. | 5/503 X |
| 2,696,963 | 12/1954 | Shepherd | 5/503 X |
| 2,719,688 | 10/1955 | Seifert | 248/188.5 |
| 2,935,286 | 5/1960 | Parsons | |
| 3,009,702 | 11/1961 | Lyon | 248/286 X |
| 3,709,556 | 1/1973 | Allard et al. | 248/125 X |
| 3,835,486 | 9/1974 | Benoit et al. | 5/503 |
| 4,262,872 | 4/1981 | Kodet | |
| 4,757,968 | 7/1988 | Kinanen et al. | |
| 4,807,837 | 2/1989 | Gawlik et al. | 248/125 |
| 4,892,279 | 1/1990 | Lafferty et al. | |
| 4,966,340 | 10/1990 | Hunter | 5/503 X |

*Primary Examiner*—David L. Talbott
*Attorney, Agent, or Firm*—Flynn, Thiel, Boutell & Tanis

[57] ABSTRACT

A mobile hospital bed has a recess and has an IV pole supported for movement from an upright position to a storage position in which a hook on the pole is disposed in the recess in order to prevent the hook from snagging clothing or other nearby objects when the IV pole is not being used. The IV pole has three telescoping sections, and two locking mechanisms which respectively releasably secure the lower and middle pole sections and the middle and upper pole sections against relative movement, each locking mechanism being controlled by a manually rotatably actuator. An arrangement separate from the locking mechanisms is provided to prevent relative rotation of the lower and middle pole sections.

10 Claims, 2 Drawing Sheets

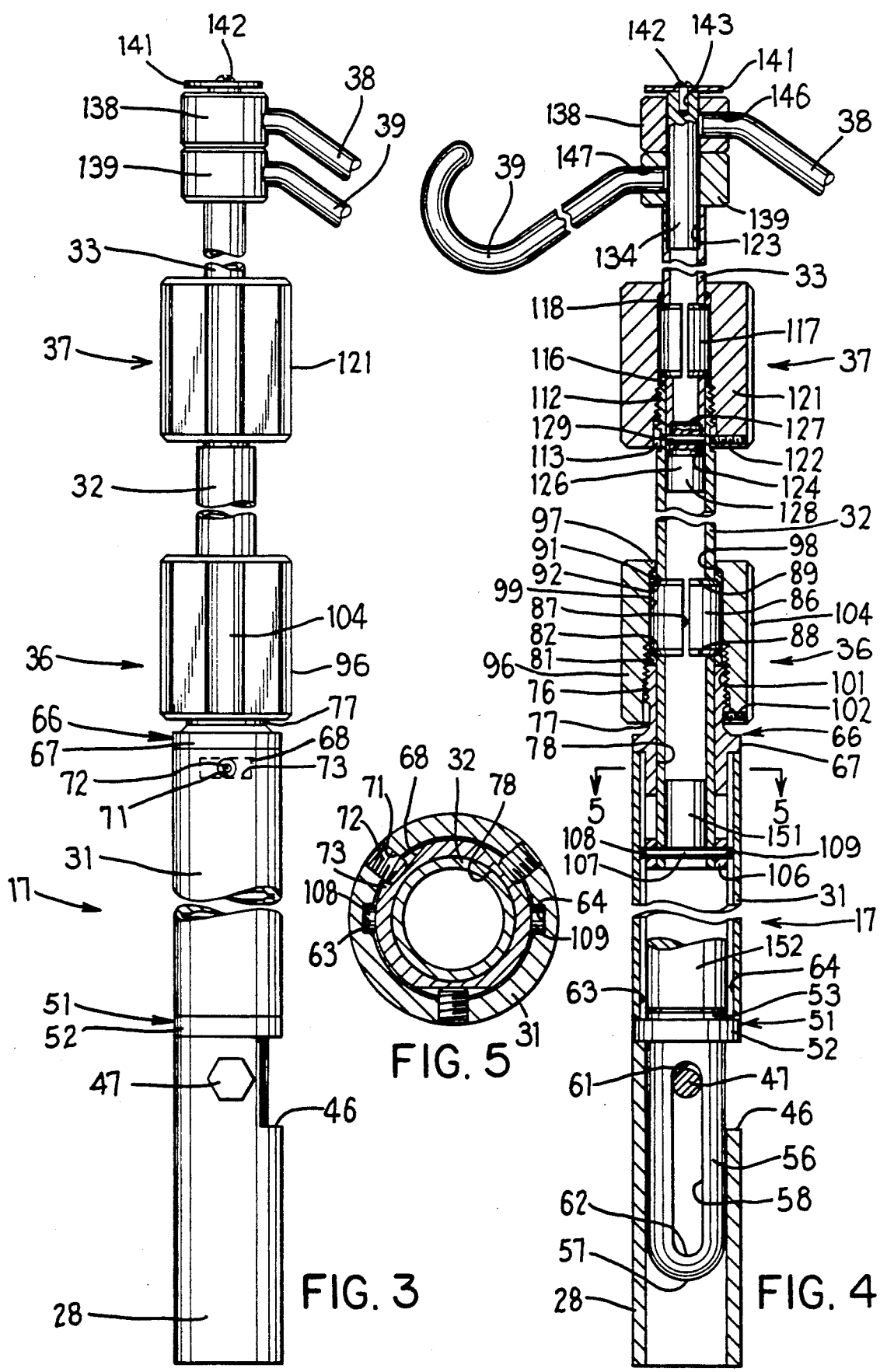

IV POLE

FIELD OF THE INVENTION

This invention relates generally to an IV pole and, more specifically, to a multi-section telescoping pole movable between an upright position and a storage position.

BACKGROUND OF THE INVENTION

For many years, medical personnel have used free-standing and bed-mounted poles which have hooks to support intravenous (IV) equipment. As to bed-mounted poles, it has been common to provide an arrangement which permits the pole to be moved from an upright position to a position extending horizontally along the side of the bed, so that when the pole is not needed it is conveniently out of the way. In order to facilitate storage of the pole, as well as to permit adjustment of its height during use, two-section poles have typically been used in which one section telescopes within the other.

Although arrangements of this type have generally been satisfactory for their intended purposes, one problem which has been encountered is that, when the pole is in its storage position extending horizontally along the side of the bed, the hooks of the pole have a tendency to snag the clothing of persons standing near the bed or to snag objects passing near a mobile bed as the mobile bed is moved.

There has been a trend to provide mobile beds with mechanisms on each side which facilitate lateral patient transfers between the mobile bed and other beds, as a result of which there is less physical room for an IV pole to be horizontally stored along the side of the bed, and it can be difficult to move the IV pole to or from its storage position when the patient transfer mechanism is in an operational configuration. Therefore, there has been a recent trend toward an arrangement in which the pole extends transversely at the end of the bed when it is in its storage position. Since a collapsed two-stage pole is typically longer than the width of the bed, this has necessitated the use of a three-stage IV pole having three telescoping sections. The hooks on these poles also have a tendency to snag clothing and objects, and in addition a further problem has developed.

More specifically, three-stage poles typically have a first locking mechanism which can releasably prevent relative lengthwise movement between the two lower pole sections and a second locking mechanism which can releasably prevent relative lengthwise movement between two upper pole sections, and a common and convenient way of actuating and deactuating the locking mechanisms is to provide a manually rotatable actuator. When attempting to tighten or release the rotatable actuator for the second (upper) locking mechanism, the middle pole section will rotate with the actuator if the actuator for the first (lower) locking mechanism is not tightened sufficiently to ensure that the middle pole section does not rotate relative to the lower pole section, which of course means that the second locking mechanism cannot be released or adequately tightened. Difficulties of this type are undesirable, particularly in medical emergency situations.

Accordingly, one object of the present invention is to provide an arrangement in which, when an IV pole is in a storage position, each hook of the pole is shielded so that the hook cannot snag clothing or other objects.

A further object is to provide a three-stage IV pole in which a rotatable actuator for the middle and upper sections can be actuated and released without any rotation of the middle section of the pole.

SUMMARY OF THE INVENTION

According to a first feature of the invention, objects and purposes of the invention are met by providing a patient support arrangement having at a first location a recess, an elongate pole having a first end supported at a second end on the patient support arrangement for movement between an operational position and a storage position, the pole having at a second end a hook and the hook being disposed in the recess when the pole is in its storage position.

According to another feature of the invention, objects and purposes of the invention are met by providing an IV pole which includes a first pole section, second and third pole sections respectively supported for lengthwise movement relative to the first and second pole sections, first and second releasable locking arrangements for respectively releasably securing the first and second pole sections and the second and third pole sections against relative lengthwise movement, the second locking arrangement including a pivotal actuator, and an arrangement cooperable with the first and second pole sections for preventing relative rotation therebetween.

BRIEF DESCRIPTION OF THE DRAWINGS

A preferred embodiment of the invention will be described in detail hereinafter with reference to the accompanying drawings, in which:

FIG. 3 is an elevational side view of the IV pole of FIG. 1;

FIG. 4 is a central sectional side view of the IV pole of FIG. 1; and

FIG. 5 is a sectional view taken along the line 5—5 in FIG. 4.

DETAILED DESCRIPTION

Figure 1:
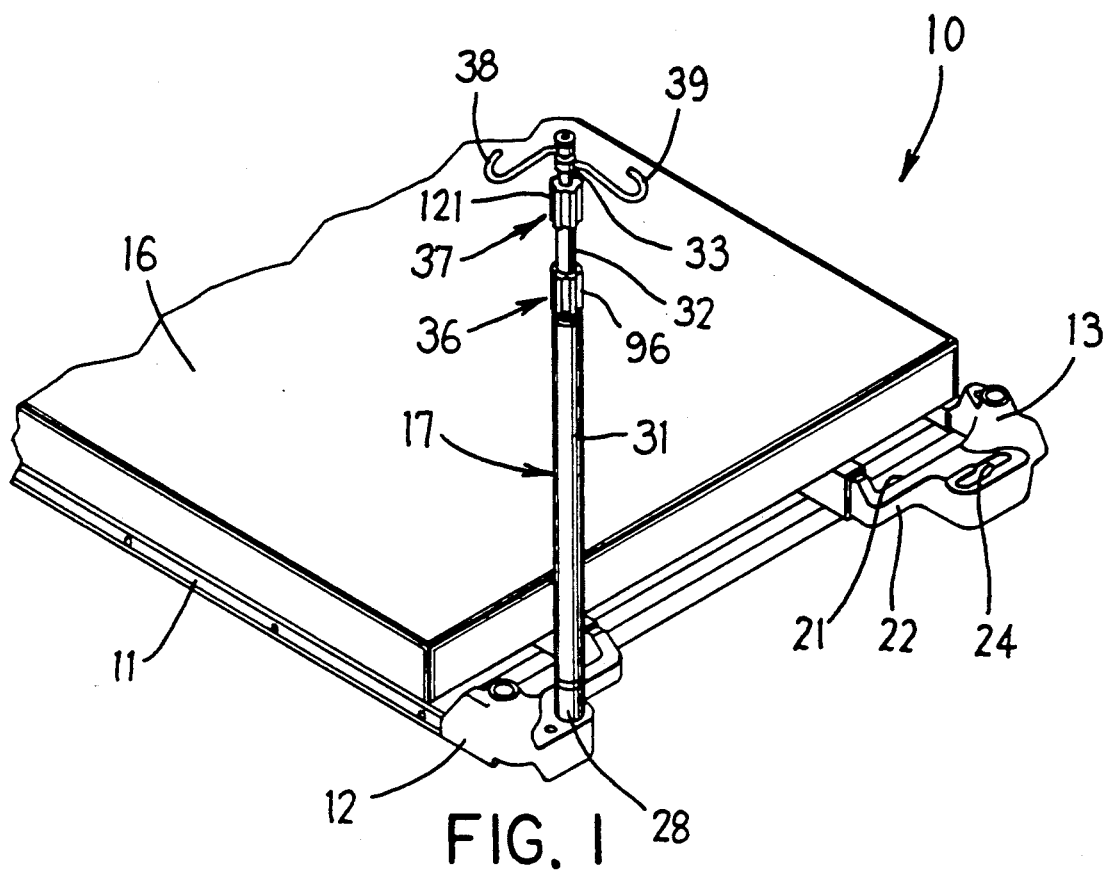
FIG. 1 is a fragmentary perspective view of part of a mobile stretcher bed embodying the present invention and having an IV pole which is shown in an upright position.
Figure 2:
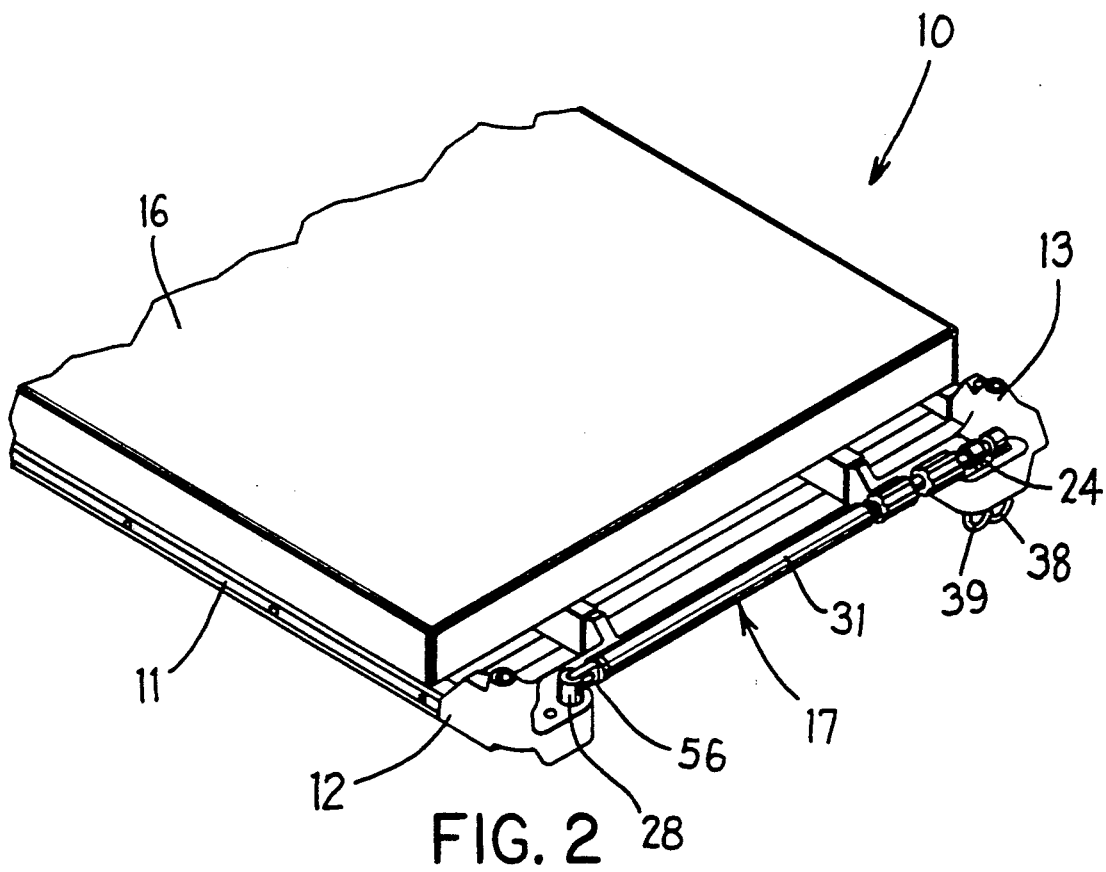
FIG. 2 is a fragmentary perspective view similar to FIG. 1 but showing the IV pole in a different operational position.

Referring to FIGS. 1 and 2, a mobile hospital stretcher bed which embodies the invention is shown at 10, and includes a frame 11 movably supported in a conventional manner by a not-illustrated wheeled base, two spaced handles 12 and 13 fixedly secured at spaced locations to one end of the frame 11, a mattress 16 resting on top of the frame 11, and an intravenous (IV) pole 17 which, as described in more detail later, is movable between an upright position shown in FIG. 1 and a storage position shown in FIG. 2.

The handles 12 and 13 are each a machined metal casting, and each have a finger slot 21 which defines a manual grip portion 22. The handle 13 has extending vertically through it a slotlike recess or pocket 24 which is elongated in a transverse direction of the stretcher 10. The other handle 12 has therethrough a cylindrical vertical hole which receives a tubular metal support sleeve 28, the sleeve 28 being fixedly secured to the handle 12 in a conventional and not illustrated manner. The sleeve 28 supports the IV pole 17 in a manner which will be described in more detail below.

As shown in FIG. 1, and as will be described later in more detail, the pole 17 includes an elongate tubular metal lower section 31, an elongate tubular metal middle section 32 which is telescopically movable within the lower section 31, and an elongate tubular metal upper section 33 which is telescopically movable within the middle section 32. The lower section 31 has at its upper end a manually operable locking mechanism 36 which can releasably secure the middle section 32 in a selected vertical position with respect to the lower section 31, and the middle section 32 has at its upper end a similar manually operable locking mechanism which can releasably secure the upper section 33 in a selected vertical position with respect to the middle section 32. The locking mechanisms 36 and 37 will also be described in more detail below. At the upper end of the upper section 33 are two hooks 38 and 39, from which medical devices such as intravenous equipment can be suspended.

The IV pole 17 and the sleeve 28 which supports it are shown in more detail in FIGS. 3 and 4. In particular, the sleeve 28 has a generally rectangular cutout extending into it from its upper edge, and a bolt 47 is disposed in holes provided in opposite walls of the tube at a location above the bottom of the cutout 46, so that the shank of the bolt 47 extends approximately diametrically across the sleeve 28.

Referring to FIG. 4, the lower end of the pole 17 is defined by a metal pivot part 51 which has near its center a radially outwardly projecting annular flange 52. Extending upwardly from the annular flange 52 is a very short cylindrical stub 53 having an outside diameter substantially equal to the inside diameter of the lower pole section 31, the stub 53 being disposed within the lower end of pole section 31 and the flange 52 being disposed against and welded to the lower end of lower tube section 31. The pivot part 51 also includes an elongate cylindrical projection 56 which extends downwardly from the flange 52 and has an outside diameter which is slightly less than the inside diameter of the sleeve 28. The outer end 57 of the projection 56 is rounded, and the projection 56 has a lengthwise slot 58 opening transversely through it, the shank of the bolt 47 being slidably received within the slot 58. As shown in FIG. 4, when the pole 17 is in its upright position the annular flange 52 rests against the upper edge of the sleeve 28, with the shank of bolt 47 near the upper end 61 of slot 58 and spaced from the lower end 62 of slot 58. Cooperation of bolt 47 and slot 58 prevent rotation of the lower pole section 31.

Referring to FIGS. 4 and 5, the lower pole section 31 has in its inner surface two diametrically opposite grooves 63 and 64 which are of rectangular cross section and which each extend the full length of the pole section 31. At the upper end of the pole section 31 is a tubular metal insert 66 having near its axial center a radially outwardly projecting annular flange 67 which rests against the upper end of the lower pole section 31. The lower portion of the insert 56 located below the flange 67 is disposed in and has an outside diameter approximately equal to the inside diameter of the upper end of pole section 31. This lower portion of insert 66 has three uniformly circumferentially spaced flats 68 (FIGS. 3 and 5), and the upper end of lower pole section 31 has three uniformly circumferentially spaced threaded holes 71 which each threadedly receive a respective setscrew 72, the inner end of each setscrew 72 engaging a respective one of the flats 68. At the lower end of each flat 68 is an upwardly facing surface 73, each setscrew 71 engaging a respective surface 73 so as to prevent upward movement of the insert 66 relative to lower pole section 31. The upper portion of the insert 66 located above flange 67 has at its upper end external threads 76, and has between threads 76 and flange 67 a portion 77 which is free of threads and has a lesser diameter than the threads 76 and flange 67. A central opening 78 through the insert 66 has a diameter only slightly larger than the outside diameter of the middle tube section 32, the middle tube section 32 being freely slidably received within the insert 66.

Referring to FIG. 4, the locking mechanism 36 includes a circular metal lock ring 81 which closely encircles the middle tube section 32, which has a downwardly facing horizontal lower axial end surface butting squarely against the horizontal upper axial end surface of the insert 66, and which has an upper axial end surface inclined to extend upwardly and outwardly. Above the lock ring 81 is a cylindrical resilient metal locking sheath 86 which has a single slit 87 extending its full axial length. The lower axial end surface 88 of the locking sheath 86 is inclined to extend upwardly and outwardly at the same angle as the edge surface 82 of ring 81, and is disposed against end surface 82 of ring 81. The upper axial end surface 89 of the sheath 86 is inclined to extend upwardly and inwardly.

Disposed above the sheath 86 is a further annular metal lock ring 91, which is identical to the lock ring 81 except that it has an inverse orientation, in particular so that an inclined axial end surface 92 thereon engages the inclined upper axial end surface 89 of the locking sheath 86.

The releasable locking mechanism 36 further includes a sleeve-like metal actuator 96 which encircles the lock rings 81 and 91 and the locking sheath 86. The actuator 96 has at its upper end a radially inwardly extending flange 97, the inner end of the flange 97 being spaced a small distance from the middle pole section 32. On the underside of the flange 97 is a surface 98 which is inclined to extend upwardly and inwardly, the radially outer edge of the inclined surface 98 engaging an upper outer axial edge of the upwardly facing horizontal axial end surface of lock ring 91. It will be recognized that the surface 98 does not need to be inclined, and could be horizontal and face directly downwardly so as to directly slidably engage the entire upper axial end surface of the lock ring 91.

The actuator 96 has extending downwardly from the outer edge of inclined surface 98 a cylindrical surface 99 which encircles and has a diameter slightly larger than the outside diameters of the lock ring 91 and locking sheath 86. Below the cylindrical surface 99 are threads which engage the threads 76 at the upper end of the tubular insert 66. A setscrew 102 is disposed in a threaded radial opening provided through the actuator 96 adjacent its lower end. The setscrew 102 is aligned with the nonthreaded portion 77 of the insert 66 and does not engage the insert 66 during normal operation. However, if an attempt is made to excessively unscrew the actuator 96 relative to the insert 66, the upward movement of actuator 96 relative to insert 66 will cause the setscrew 102 to eventually engage the lowermost of the threads 76 on insert 66 and thus prevent further upward movement of actuator 96, thereby preventing its removal from the insert 66. The exterior of the actuator 96 is knurled as indicated at 104, in order to facilitate a firm manual grasp of the actuator 96.

Referring to FIG. 4, an annular metal tube stop 106 closely encircles the lower end of the middle tube section 32, its inside diameter being approximately equal to the outside diameter of the tube 32 and its outside diameter being slightly less than the inside diameter of the lower tube section 31, the outer surface of the tube stop 106 slidably engaging the inner surface of the lower tube section 31. A cylindrical metal pin 107 extends through aligned radial openings provided in the tube stop 106 and the lower end of middle tube section 32, the ends 108 and 109 of the pin 107 each being slidably disposed in a respective one of the grooves 63 and 64 in the inner surface of lower pole section 31, as best shown in FIG. 5, thereby preventing any rotation of the middle tube section 32 relative to the lower tube section 31.

The upper end of the middle pole section 32 has external threads 112, and immediately below threads 112 is a non-threaded surface portion having a diameter slightly less than the diameter of the rest of the middle tube section 32.

The releasable locking mechanism 37 provided at the upper end of the middle tube section 32 includes a lock ring 116, locking sheath 117, lock ring 118, actuator 121 and setscrew 122, which are respectively similar in structure and function to the corresponding components of releasable locking mechanism 36 and are therefore not described in detail.

The central opening through the upper pole section 33 has at its upper and lower ends respective portions 123 and 124 of increased diameter. A plastic tube stop 126 is provided at the lower end of the upper pole section 33, and has a cylindrical upper portion which is disposed in and has a diameter approximately equal to that of the increased diameter portion 124 of the central opening through upper pole section 33. The tube stop 126 also has a cylindrical lower portion 128 which is disposed immediately below the lower end of the upper pole section 33, which has an outside diameter approximately equal to the outside diameter of upper pole section 33, and which slidably engages the inner surface of the middle pole section 32. A cylindrical metal pin 129 extends radially through aligned openings in the walls of upper tube section 33 and in upper portion 127 of tube stop 126, in order to connect tube stop 126 to the upper pole section 33. The outer ends of the pin 129 do not extend beyond the cylindrical outer surface of upper pole section 33.

A cylindrical metal collar pin 134 has its lower end press fit into the increased diameter portion 123 of the central opening through upper pole section 33. Two annular metal collars 138 and 139 closely encircle and are freely rotatable on the collar pin 134. A washer 141 is disposed against and extends radially outwardly beyond the upper end of the collar pin 134, and is fixedly held in place by a screw 142 which engages a threaded axial opening 143 provided in the upper end of collar pin 134. The washer 141 limits upward movement of the collars 138 and 139, and the upper end of upper pole section 33 limits downward movement of the annular collars 138 and 139.

The collars 138 and 139 have respective radial holes 146 and 147 therein, which each receive the radially inner end of a respective one of the metal hooks 38 and 39, the inner end of each hook being welded to the associated collar.

A cylindrical stop plug 151 is disposed within the lower end of middle tube section 32, and is preferably made of rubber or plastic. The outside diameter of stop plug 151 is preferably a little less than the inside diameter of the tube section 32, so that the stop plug 151 can slide within the tube section 32 to facilitate its insertion during assembly. The lower end of the stop plug 151 engages the pin 107. A similar cylindrical stop plug 152 is disposed in the lower portion of lower tube section 31, the lower end of stop plug 152 engaging the upper end of the cylindrical stub 53 on pivot part 51.

OPERATION

The operation of the locking mechanism 36 will be described first. Referring to FIG. 4, when the actuator 96 is manually rotated in a first rotational direction which causes it to move downwardly relative to insert 66 and lower pole section 31, the flange 97 on actuator 96 urges the lock ring 91 to move downwardly toward the lock ring 81, lock ring 81 being stationary because of its engagement with the upper end of the insertion 66. Thus, the locking rings 91 and 81 exert axial compressive forces on the locking sheath 86. Due to engagement of the inclined axial end surfaces 82 and 92 on lock rings 81 and 91 with the inclined axial end surfaces 88 and 89 on locking sheath 86, the walls of the locking sheath 86 are urged radially inwardly, as a result of which the effective inside diameter of the locking sheath 86 decreases while the width of the slit 87 therein decreases. The inner surface of the locking sheath 86 thus moves into progressively tighter frictional engagement with the exterior surface of middle tube section 32, until the friction is sufficient to prevent vertical movement of the middle tube section 32 relative to lower tube section 31. In order to release the locking mechanism 36, the actuator 96 is rotated away from the locking position which established this level of friction in a second rotational direction opposite the first rotational direction to a release position, the actuator 96 moving upwardly relative to insert 66 so that the axial compressive force exerted by rings 91 and 81 on locking sheath 86 decreases and the locking sheath 86, through its inherent resilience, returns to its original shape and diameter, at which friction between the locking sheath 86 and middle pole section 32 is minimal and the middle pole section 32 can be freely moved relative to the insert 66 and lower pole section 31.

Locking mechanism 37 is operated in a manner similar to mechanism 36, and its operation is therefore not described in detail. However, it is important to note that, in order to rotate its actuator 121 into and out of its locking position, the middle pole section 32 must be prevented from rotating, which is achieved here through the engagement of the ends 108 and 109 of pin 107 on middle pole section 32 with the grooves 63 and 64 in the inner surface of lower pole section 31, the lower pole section 31 in turn being prevented from rotating by the cooperation between slot 58 of pivot part 51 and the shank of bolt 47 in the sleeve 28 secured to the stretcher 10 It should be noted that the locking mechanism 37 can be secured and released even when locking mechanism 36 is completely released, because pin ends 108 and 109 and grooves 63 and 64 prevent relative rotation of pole sections 31 and 32 even when locking mechanism 36 is completely released.

When the IV pole 17 is in the upright position shown in FIG. 1, the actuator 96 can be manually grasped and moved to its release position, the middle pole section 32 can be manually moved to a selected vertical height, and then the actuator 96 can be rotated to its locking position in order to releasably lock the pole section 32 in the selected position. Tube stop 106 will, if necessary, engage the lower end of insert 66 to prevent middle tube section 32 from being pulled out of lower tube section 31. Then, the actuator 121 can be manually grasped and rotated to its release position, the upper pole section 33 can be moved to a selected vertical position, and the actuator 121 can be rotated back to its locking position to releasably secure the upper pole section 33 in the selected position. Then, the hooks 38 and 39 can each be rotated to any desired angular position and used to support any appropriate conventional medical apparatus.

After use, the height of IV pole can be reduced by manually rotating each of the actuators 96 and 121 to the release position, and lowering the pole sections 32 and 33 until the tube stop 126 (FIG. 4) at the lower end of upper pole section 33 engages the stop plug 151 in the lower end of middle pole section 32, and the tube stop 106 at the lower end of middle pole section 32 engages the stop plug 152 in the end of lower pole section 31.

Thereafter, in order to move the pole 17 to its storage position, the lower pole section 31 is manually grasped and lifted so that, as shown in FIG. 4, the pivot part 51 moves upwardly until the shank of bolt 47 on sleeve 28 is disposed at the lower end 62 of the slot 58. While maintaining the shank of bolt 47 near the lower end 62 of slot 58, the pole is pivoted about the axis of bolt 47 from an upright position to the storage position shown in FIG. 2, in which the pivot part 52 extends horizontally outwardly away from the bolt 47 through the cutout 46 in the side of sleeve 28, and in which the upper end of IV pole 17 rests on top of the handle 13. During this pivoting movement, the force of gravity causes the hooks 38 and 39 to automatically pivot to a position in which they are adjacent each other and each hang downwardly from the upper end of the pole, the hooks thus automatically pivoting to positions in which they will automatically move into the recess 24 in the handle 13 as the pole is pivoted. When the hooks 38 and 29 are in the recess 24 in handle 13, the handle 13 effectively prevents clothing or other objects from being snagged by the hooks as the stretcher 10 is moved.

It is not unusual for two different models of a hospital stretcher to have respective widths. Thus, referring to FIG. 1, the distance between handles 12 and 13 would be different on the two models. The stop plugs 151 and 152 used for a given bed model have selected axial lengths which ensure that, when the pole 17 is fully vertically collapsed, its axial length will be that needed to cause hooks 38 and 39 to be aligned with and move directly into recess 24 as the pole is pivoted to its storage position. For the bed model with the smallest width, the stop plugs 151 and 152 can be completely omitted if the resulting collapsed pole length corresponds to the spacing between handles 12 and 13 on that bed model.

In order to move the pole 17 from the storage position of FIG. 2 to the upright position of FIG. 1, the lower tube section 31 is manually grasped and pivoted upwardly about bolt 47 until the slot 48 in pivot part 51 is substantially vertical, and then the pole 17 is moved downwardly while the shank of bolt 47 slides upwardly within slot 58 until the annular flange 52 on pivot part 51 is resting against the upper end of the sleeve 28, as shown in FIG. 1.

Although a single preferred embodiment of the invention has been shown in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An apparatus comprising: patient support means having at a first location thereon an upwardly facing surface and a recess opening downwardly into said patient support means through said upwardly facing surface, and an elongate pole having first and second ends and supported at said first end at a second location on said patient support means spaced from said first location for movement between an operational position and a storage position, said pole having at said second end thereof a hook; wherein said hook is disposed in said recess and said second end of said pole rests on said upwardly facing surface when said pole is in said storage position; and wherein said hook is freely rotatably supported on said pole and in response to gravity automatically rotates into alignment with and moves into said recess as said pole moves from said operational to said storage position.

2. An apparatus of claim 1, wherein said pole includes first and second elongate pole sections supported for relative lengthwise movement, and locking means for releasably securing said pole sections against relative lengthwise movement, said first end of said pole being one end of said first pole section and said second end of said pole being an end of said second pole section, and including stop means for halting downward movement of said second pole section relative to said first pole section in a position in which said pole has an effective length causing said hook to be aligned with and to move into said recess in said patient support means as said pole is moved to its storage position.

3. An apparatus of claim 2, wherein said stop means includes a stop plug disposed within said first pole section adjacent said first end of said pole and engageable with an end of said second pole section remote from said second end of said pole.

4. An apparatus of claim 2, wherein said locking means has a locked state releasably securing said pole sections against relative lengthwise movement and has a released state permitting relative lengthwise movement of said pole sections, said locking means being in said released state when said pole is in said storage position.

5. An apparatus of claim 1, wherein said elongate pole includes an elongate first pole section having at an end thereof said first end of said pole; an elongate second pole section supported on said first pole section for lengthwise movement relative thereto; an elongate third pole section supported on said second pole section for lengthwise movement relative thereto and having at an end thereof said second end of said pole; first releasable locking means for releasably securing said second pole section against said lengthwise movement relative to said first pole section; second releasable locking means for releasably securing said third pole section against lengthwise movement relative to said second pole section, said second locking means including a manual actuating part supported for pivotal movement between first and second positions about an axis extending approximately parallel to said pole and means for respectively permitting and preventing lengthwise movement of said third section relative to said second section when said actuating part is respectively in said first and second positions; and means cooperable with said first and second pole sections for preventing relative rotation therebetween.

6. An apparatus of claim 5, wherein said means for preventing relative rotation includes said first pole section having an axially extending groove in an inner surface thereof and said second pole section having a radially projecting portion which is slidably received in said groove.

7. An apparatus of claim 6, wherein said first pole section has a further groove in said inner surface thereof which is diametrically opposed to said first-mentioned groove, and wherein said second section has extending radially therethrough a pin having first and second ends, said first end of said pin being said radially projecting portion slidably disposed in said first-mentioned groove, and said second end of said pin being slidably disposed in said further groove.

8. An apparatus comprising: patient support means having at a first location thereon an upwardly facing surface and a recess opening downwardly into said patient support means through said upwardly facing surface, and an elongated pole having first and second ends and supported at said first end at a second location on said patient support means spaced from said first location for movement between an operational position and a storage position, said pole having at said second end thereof a hook, wherein said hook is disposed in said recess and said second end of said pole rests on said upwardly facing surface when said pole is in said storage position; and wherein said hook is movably supported on said pole and automatically moves into said recess as said pole moves from said operational to said storage position, wherein said pole extends approximately horizontally in said storage position, wherein said hook is freely rotatably supported on said pole for movement about a pivot axis which is approximately parallel to a central axis of said pole, and wherein as said pole is moved from said operational position to said storage position said hook is automatically pivoted about said pivot axis by gravity to a hanging position in which it is aligned with said downwardly opening recess in said patient support means.

9. An apparatus of claim 8, including a further hook freely pivotally supported on said pole adjacent said first-mentioned hook for movement about said pivot axis independently of said first-mentioned hook, said further hook being received in said recess in said patient support means as said pole is moved to its storage position.

10. An apparatus comprising: patient support means having at a first location thereon an upwardly facing surface and a recess opening downwardly into said patient support means through said upwardly facing surface, and an elongate pole having first and second ends and supported at said first end at a second location on said patient support means spaced from said first location for movement between an operational position and a storage position, said pole having at said second end thereof a hook; wherein said second end of said pole rests on said upwardly facing surface when said pole is in said storage position; wherein said hook is freely rotatably supported on said pole and in response to gravity automatically rotates into alignment with and moves into said recess as said pole moves from said operational to said storage position; and wherein said pole includes: an elongate first pole section; an elongate second pole section supported on said first pole section for lengthwise movement relative thereto; an elongate third pole section supported on said second pole section for lengthwise movement relative thereto; first releasable locking means for releasably securing said second pole section against lengthwise movement relative to said first pole section; second releasable locking means for releasably securing said third pole section against lengthwise movement relative to said second pole section, said second locking means including a manual actuating part supported for pivotal movement between first and second positions about an axis extending approximately parallel to said pole and means for respectively permitting and preventing lengthwise movement of said third pole section relative to said second pole section when said actuating part is respectively in said first and second positions; and means cooperable with said first and second pole sections for preventing relative rotation therebetween, said first end of said pole being an end of said first pole section and said second end of said pole being an end of said third pole section.

* * * * *